United States Patent [19]

Clarke et al.

[11] Patent Number: 4,968,303
[45] Date of Patent: Nov. 6, 1990

[54] HYPODERMIC SYRINGE HOLDER

[75] Inventors: John W. Clarke, Indianapolis; Dale C. Harris, Fairland, both of Ind.

[73] Assignee: Eli Lilly and Company, Indianapolis, Ind.

[21] Appl. No.: 249,799

[22] Filed: Sep. 27, 1988

[51] Int. Cl.⁵ .............................................. A61M 5/00
[52] U.S. Cl. ................................. 604/187; 604/218; 604/233; 604/228
[58] Field of Search ............... 604/181, 187, 184, 218, 604/232, 233, 218, 228

[56] References Cited

U.S. PATENT DOCUMENTS

| | | |
|---|---|---|
| 1,512,294 | 10/1924 | Marcy . |
| 1,606,034 | 11/1926 | MacGregor . |
| 1,718,596 | 6/1929 | Smith . |
| 1,757,809 | 5/1930 | Montuori . |
| 2,074,401 | 3/1937 | Kauzal . |
| 2,748,767 | 6/1956 | Wright . |
| 2,859,751 | 11/1958 | Stroop . |
| 2,871,858 | 2/1959 | Dann et al. . |
| 3,548,826 | 12/1970 | Wilson . |
| 3,682,175 | 8/1972 | Halter . |
| 4,014,331 | 3/1977 | Head ................................. 604/187 |
| 4,020,838 | 5/1977 | Phillips et al. . |
| 4,033,346 | 7/1977 | Phillips et al. ...................... 604/208 |
| 4,512,767 | 4/1985 | Denance ......................... 604/208 X |
| 4,576,591 | 3/1986 | Kaye et al. ..................... 604/208 X |
| 4,594,073 | 6/1986 | Stine ................................... 604/187 |
| 4,643,724 | 2/1987 | Jobe .................................. 604/232 |
| 4,687,472 | 8/1987 | Gross . |
| 4,744,789 | 5/1988 | Johnson ............................... 604/218 |

FOREIGN PATENT DOCUMENTS

| | | | |
|---|---|---|---|
| 1566642 | 3/1970 | Fed. Rep. of Germany ...... | 604/232 |
| 3048761 | 7/1982 | Fed. Rep. of Germany ...... | 604/187 |
| 3408618 | 9/1985 | Fed. Rep. of Germany ...... | 604/232 |
| 8401509 | 4/1984 | Int'l Pat. Institute .............. | 604/187 |

*Primary Examiner*—Robert Bahr
*Assistant Examiner*—Jennifer L. Doyle
*Attorney, Agent, or Firm*—Donald R. Stuart; Leroy Whitaker

[57] ABSTRACT

A syringe holder for administering the contents of pre-filled cartridge-cannula units comprises generally a cartridge holding barrel rotatably connected to a push rod guiding sleeve, and a push rod slidably mounted in the sleeve.

5 Claims, 2 Drawing Sheets

HYPODERMIC SYRINGE HOLDER

BACKGROUND OF THE INVENTION

This invention relates to hypodermic syringes, and more specifically to a hypodermic syringe body adapted for delivering viscous liquids from prefilled cartridge-cannula units.

Bovine somatotropin (BST) is under development by several companies as an agent for increasing milk production efficiency of dairy cows. A particularly good vehicle for delivery of BST is the injectable sustained release formulation disclosed in U.S. patent application Ser. No. 06/768,605. The formulation is a viscous liquid comprising BST suspended in a carrier comprising from about 1% to about 20% wax and from about 80% to about 99% of oil. The present invention arose from the need to provide a reliable and convenient system for administering this formulation.

To minimize the risk of cross contamination between animals, an administration system utilizing disposable prefilled cartridges with attached cannulas was desired. A problem arose with existing technology in that there was a tendency to excess breakage of cannulas from the cartridges. Excess splitting of the cartridges was also experienced. These problems arose due to the viscous character of the formulation, requiring that a great deal of pressure be put on the syringe's plunger to administer the drug. The fact that the drug must be refrigerated between the point of manufacture and the point of use exacerbates this problem.

SUMMARY OF THE INVENTION

The present invention provides a syringe holder adapted to be used with a disposable prefilled cylindrical cartridge-cannula unit comprising:

a cartridge holding barrel having a cylindrical bore that is adapted to hold the cartridge, the barrel being open at one end for receiving the cartridge and partially closed at the opposite end by an end wall that limits axial movement of the cartridge, the barrel having an extension on the partially closed end, which extension has a cylindrical bore coaxial with the bore of the barrel, the extension's bore being of sufficiently large diameter so that the cannula and sheath of the cartridge can pass freely through it but of adequately restricted diameter to prevent excessive angular displacement of the cannula, thereby preventing the cannula from breaking from the cartridge, a push rod guiding sleeve, a push rod slidably mounted in the sleeve, and hinge means connecting the barrel to the push rod guiding sleeve so that the barrel can be rotated between an operation position in which its bore is coaxial with the push rod and a loading position in which the bore of the barrel is unobstructed, the push rod guiding sleeve including a partially open extension disposed adjacent to the open end of the barrel when in the operation position, the open section defining undercuts adapted to receive the exposed plunger end of the cartridge with a snap fit when the barrel is rotated into operation position, thereby preventing unintended rotation of the cartridge out of the operation position

DESCRIPTION OF THE PREFERRED EMBODIMENTS

Figure 1:
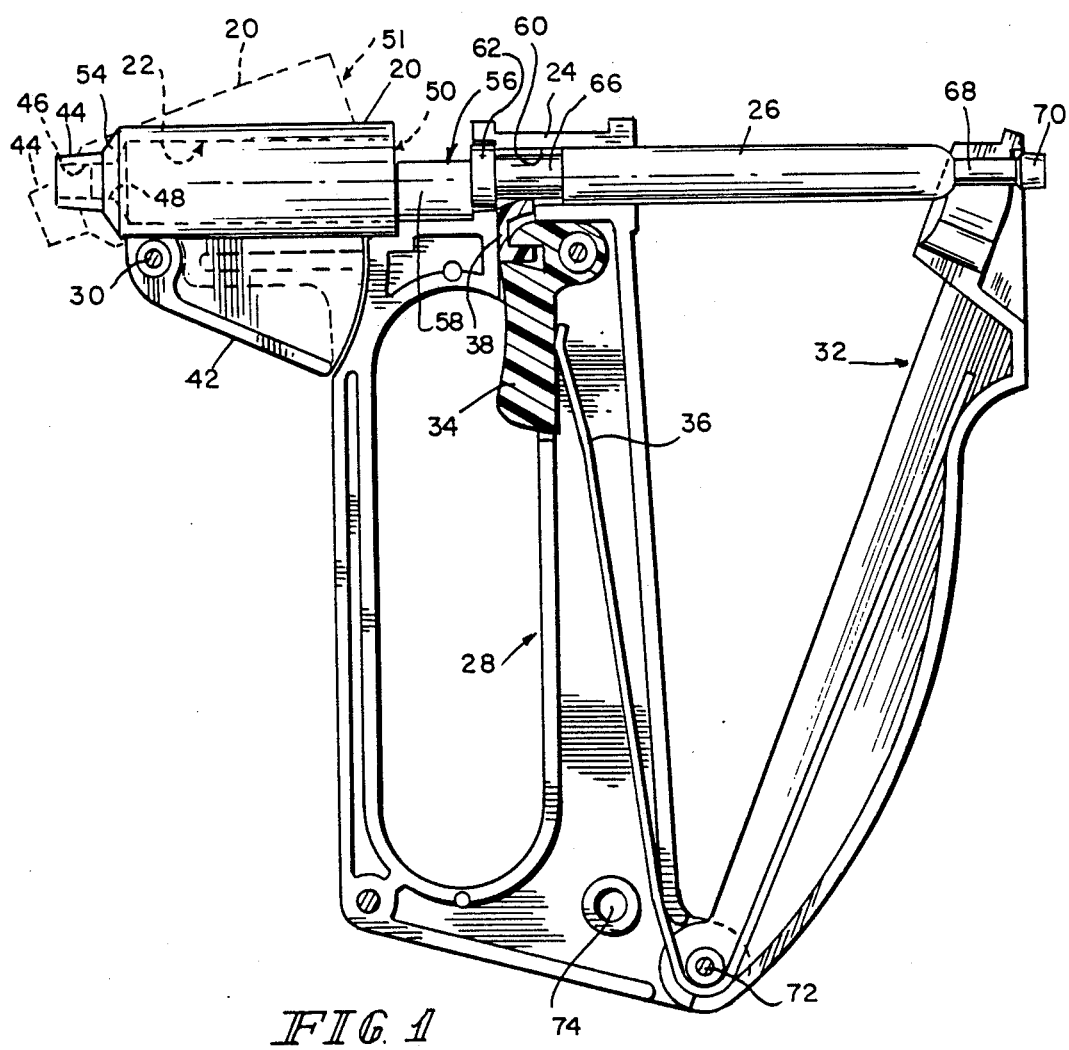
FIG. 1 is a longitudinal section of a syringe cartridge holder of the invention.
Figure 3:
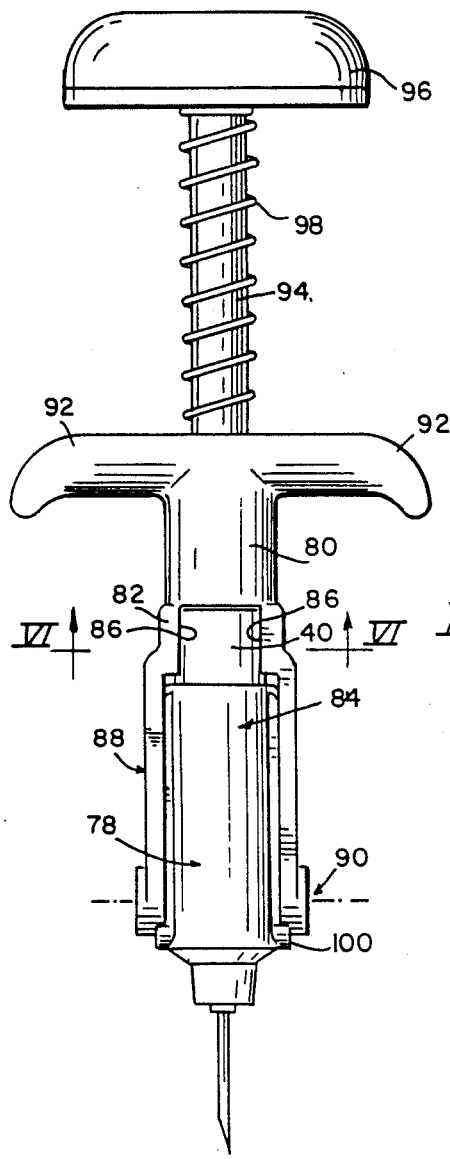
FIG. 3 is a top plane view of the embodiment illustrated in FIG. 2.
Figure 2:
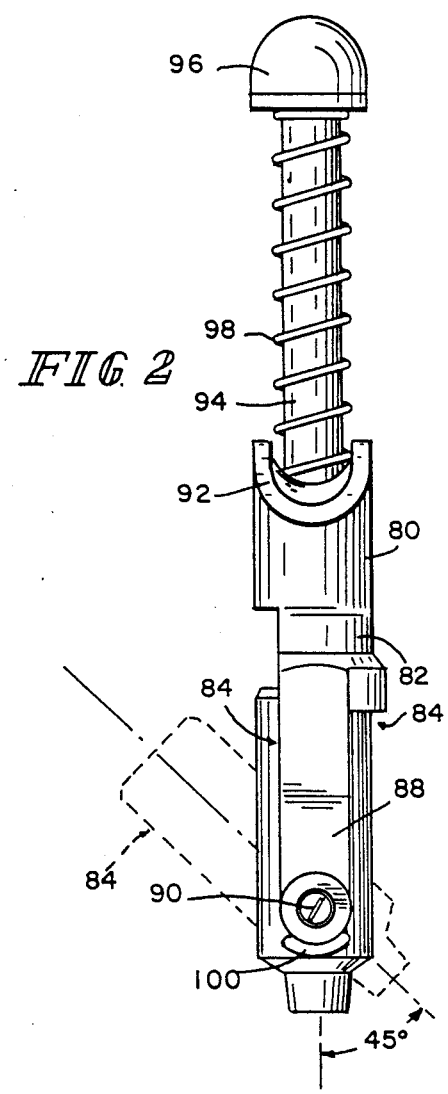
FIG. 2 is a side elevation of an alternative embodiment of a syringe cartridge holder of the invention.

In a preferred embodiment, illustrated in the drawings, the invention provides a system for administering a drug compound suspended in a viscous liquid. The system uses a prefilled, disposable, cartridge-cannula unit 1 (FIGS. 4 and 5) with a syringe holding device of the invention. A gun style holding device is illustrated in FIG. 1, and an alternative syringe style injection device is illustrated in FIGS. 2 and 3. The system is particularly adapted for giving subcutaneous injections to cattle.

Figure 5:
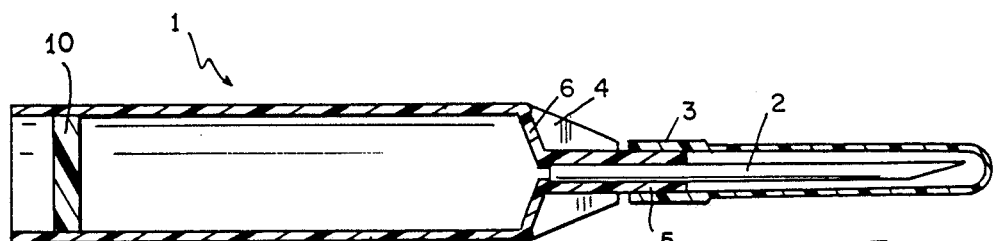
FIG. 5 is a longitudinal section of the cartridge shown in FIG. 4.
Figure 4:
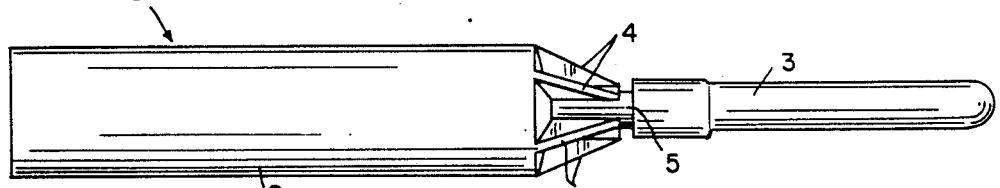
FIG. 4 is a side elevation of a cartridge of the type used in the devices of FIGS. 1 to 3.

Referring generally to FIGS. 4 and 5, the design of the cartridge 1 is based on several requirements. Since the drug compound must be kept refrigerated between the point of manufacture and the point of use, the cartridge was made without finger flanges and without a plunger rod to minimize the storage space required In order to minimize the risk of cross contamination between animals, disposable cartridges 1 are used that have the cannula 2, required for the injection, preattached and covered with a sheath 3. The sheath maintains sterility and protects the sharp cannula. As an aid to sheath removal and as a means of reinforcing the cannula hub, there are six radial ribs 4 located at the junction between the hub 5 and the end wall 6 of the cartridge These ribs will be discussed further during the description of the gun and syringe injection devices The cartridge is desirably molded of, for example, polypropylene.

The gun style injection device of FIG. 1 consists generally of a cartridge holding barrel 20 with a cylindrical bore 22, a push rod guiding sleeve 24, a push rod 26 slidably mounted in the sleeve, a body 28 carrying the push rod guiding sleeve, and providing a grip for holding the device, a pivot point 30 connecting the barrel 20 to the push rod guiding sleeve 24 via the body so that the cartridge holder sleeve can be rotated between an operation position in which the bore of the barrel is coaxial with the push rod and a loading position in which the bore of the barrel is unobstructed, a handle 32 mounted at one end on the gun body at a pivot point and at the other end to the push rod for applying pressure to slide the push rod, and a trigger mechanism comprising a trigger 34, spring 36 and sear 38 for stopping premature movement of the push rod 26.

One significant feature of the "gun" style injection device of FIG. 1 relating to its use with the cartridge 1 is the swing out barrel 20 which serves as a holder for the cartridge The sidewalls 8 of a cartridge in the barrel are in close proximity to the walls of the bore 22 for all but a short exposed length 40 (not seen in FIG. 1, but a corresponding arrangement is shown in the embodiment of FIG. 3 and in detail in FIG. 6–8) at the plunger end of the cartridge. This prevents splitting of the cartridge when pressure is applied to the plunger 10 of the cartridge The barrel 20 is attached to the body 28 of the device at a pivot point 30. To assist in rotating the barrel to the loading position, a lever 42, which is molded as a part of the barrel extends below the body. The barrel 20 has an extension 44 on its partially enclosed end The extension serves two purposes: to minimize the angular displacement of the cannula 2, thereby preventing the cannula from breaking off the cartridge 1, and to prevent the cartridge from rotating, so the sheath can be removed from the cannula with a twisting action More specifically, to restrict excessive angular displacement of the cannula, the extension 44 has a cylindrical bore 46 coaxial with the bore of the barrel 20. The diameter of the extension's bore 46 is sufficiently large to allow the cannula 2 and sheath 3 to pass freely, but is adequately restricted to prevent excessive angular displacement of the cannula 2 and hub 5. It is desirable to limit angular deflection of the cannula and hub to no more than about 15°. The length of the extension is typically from ⅛ to ½ the length of the cannula.

To prevent rotation of the cartridge, the extension has on its interior six slots 48 that are engaged by six ribs 4 located around the cannula hub of the cartridge.

In use, the lever 42 is pushed up to swing the open end of the barrel 50 out of alignment with the push rod guiding sleeve 24 so that the open end of the barrel 50 is unobstructed. In FIG. 1 the barrel is shown in the loading position at 51. The cartridge 1 is inserted, with the cannula sheath in place, cannula end first, into the barrel The sheath passes through the hole 52 in the partially closed end 54 of the barrel, the ribs 4 on the cartridge engage the slots 48 in the barrel, and finally the closed end 6 of the cartridge seats against the bottom of the inside of the barrel 20. The barrel, now containing the cartridge, is then moved into operation position by rotating the barrel into alignment with the push rod 26. When this is done, the exposed portion 40 of the plunger end of the cartridge flexes and "snaps" into the under-cuts 56 defined by the undercuts 86 detailed in FIGS. 4–8 correspond to the undercuts 56 of the embodiment of FIG. 1 partially open extension 58 of the push rod guiding sleeve. When the injection is to be given, the sheath 3 covering the cannula 2 is removed. Sheath removal is easier and safer if the sheath can be "twisted" while it is being pulled off. The cartridge is prevented from turning as the sheath is twisted by its six ribs 4 which are in contact with the six slots 48 inside of the barrel extension. It will be clear to those skilled in the art that other cooperating intermeshing means equivalent to the ribs and slots illustrated can also be used to stop rotation of the cartridge.

Another significant feature of the injection gun, illustrated in FIG. 1, is the action of the push rod 26 and trigger mechanism. The push rod is retained in the push rod guiding sleeve 24 which is behind and coaxial with the barrel. The forward end of the push rod is retained in the bore 60 of the push rod sleeve by a head 62 which is larger than the shaft 64 of the rod and larger than the bore of the sleeve. This head has a diameter slightly smaller than the inside diameter of the cartridge 1. To provide a catch for the trigger mechanism, just behind the head 62 is a section 66 of the push rod with a diameter smaller than the main shaft of the rod. The length of this section is equal to the width of the sear 38 plus approximately 3/16 inch. The shaft of the rod is free to slide back and forth in the bore of the push rod sleeve. This bore is coaxial with the bore of the cartridge holding sleeve.

To pivotally fasten the back end of the push rod shaft to the handle 32, the back end of the shaft 64 has a section 68 of reduced diameter, and the shaft then ends by increasing this smaller diameter for a short section This short section of the rod passes through a "keyhole" slot 70 in the top end of the gun's pivoting handle. The bottom end of the handle is attached at a pivot point 72 which extends from the base of the gun body. The back of this handle is curved to fit the palm of a hand.

The sear 38, which is attached to the trigger 34, allows the head of the push rod to move forward into the open end of the cartridge without making contact with the rubber plunger 10 that closes the open end of the cartridge this helps to stabilize the cartridge in the gun while making an injection. Once the cannula has penetrated the required depth for an injection, the trigger 34 is pulled to move the sear 38 away from the catch 66 in the plunger rod. The push rod can then be moved forward, by squeezing the pivoting handle 32 toward the gun body, until the rubber plunger 10 in the cartridge has forced all of the compound to be injected out through the cannula 2.

An additional feature on the gun is a hole 74 provided through both sides of the body. This hole can be used to retain the cannula sheath 3 once it has been removed from the cartridge. This allows the user, who wishes to place the sheath back on the cartridge after the injection has been made, to retain the sheath and still keep a hand free to use during the injection.

The syringe style holding device of FIGS. 2 and 3 comprises generally a cartridge holding barrel 78, a push rod guiding sleeve 80 with a partially open extension 82 adjacent to the open end 84 of the barrel defining undercuts 86 to afford a snap fit with the cartridge, and a yoke 88 which connects push rod guiding sleeve 80 to the barrel 78 at a pivot point 90, finger flanges 92, a push rod 94, a push rod handle 96, and a push rod return spring 98.

Figures 6, 7, 8:
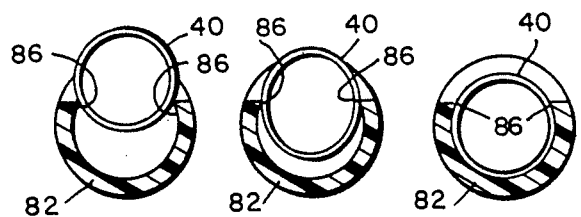
FIG. 6 is a view along line VI—VI of GIG 3, showing the cartridge in the operation position
FIG. 7 is a view identical to FIG. 6, but with the cartridge shown in the loading position.
FIG. 8 is a view identical to FIG. 6, but with the cartridge shown flexing into the operation position.

The syringe style device of FIGS. 2 and 3 also has a swing out cartridge holding barrel 78 which serves the same purpose as and has similar features to the barrel 20 of the gun device of FIG. 1. This barrel has a raised arc 100 on either side, adjacent to the pivot points, which serve to restrict the swing of the barrel so that it always stays on the "loading" side of the yoke. Both the gun and the syringe injectors take advantage of the ability of the open end of the cartridge to flex and "snap" in under large undercuts, as illustrated in FIGS. 6 to 8.

The syringe holding devices of the invention are preferably molded of, for example, polycarbonate, but can also be fabricated using a suitable metal.

We claim:

1. A syringe body adapted to be used with a prefilled cylindrical cartridge-cannula unit comprising:
    a cartridge holding barrel having a cylindrical bore in its main body that is adapted to hold the cartridge, the barrel being open at one end for receiving the cartridge and partially closed at the opposite end by an end wall that limits axial movement of the cartridge, the barrel having an extension on the partially closed end, which extension has a cylindrical bore coaxial with the bore of the barrel, the extension's bore being of sufficiently large diameter so that the cannula and sheath of the cartridge can pass freely through it but of adequately restricted diameter to prevent excessive angular displacement of the cannula, thereby preventing the cannula from breaking from the cartridge, a push rod guiding sleeve, a push rod slidably mounted in the sleeve, and hinge means connecting the cartridge holding barrel to the push rod guiding sleeve so that the barrel can be rotated between an operation position in which its bore is coaxial with and opposed to the push rod and a loading position in which its bore is unobstructed, the push rod guiding sleeve including a partially open extension disposed adjacent to the open end of the barrel when in the operation position, the partially open section defining undercuts adapted to receive the exposed, plunger end, of the cartridge with a snap fit when it is rotated into operation position, thereby preventing unintended rotation of the cartridge out of the operation position.

2. The syringe holder of claim 1 wherein the extension on the barrel limits the angular deflection of the cannula to no more than 15 degrees from the axis of the cartridge.

3. The syringe holder of claim 1 wherein the push rod guiding sleeve is carried on a piston grip body.

4. The syringe holder of claim 1 in combination with a cartridge-cannula unit having a cannula hub connecting the cannula to the cartridge, the interior surface of the extension on the barrel and the hub of the cartridge-cannula unit having intermeshing means for preventing rotation of the cartridge.

5. The device of claim 4 wherein the intermeshing means comprise at least one rib on the hub of the cannula and a corresponding slot on the bore of the extension.

* * * * *